United States Patent [19]

Kursar

[11] Patent Number: 5,174,292
[45] Date of Patent: Dec. 29, 1992

[54] HAND HELD INTRAOCULAR PRESSURE RECORDING SYSTEM

[76] Inventor: Gerald H. Kursar, Des Peres Square, 12710 Manchester Rd., Des Peres, Mo. 63121

[21] Appl. No.: 774,825

[22] Filed: Oct. 11, 1991

[51] Int. Cl.⁵ .............................................. A61B 3/16
[52] U.S. Cl. .................................... 128/645; 128/652
[58] Field of Search ............... 128/645, 646, 650, 651, 128/652

[56] References Cited

U.S. PATENT DOCUMENTS 3,150,521  9/1964  Mackay et al. ...................... 128/645
3,564,907  2/1971  Holcomb et al. .................... 128/645
4,951,671  8/1990  Coan .................................. 128/652

Primary Examiner—Randy C. Shay
Attorney, Agent, or Firm—Eugene E. Renz, Jr.

[57] ABSTRACT

A hand held portable tonometer device for monitoring the intraocular pressure in an eye through the sclera. The device has a tubular frame having an axis and forming a handle by which the device is held. The handle includes a pressure transducer for generating intraocular pressure measurements upon contact of a scleral probe on the eye to cause a scleral indentation and to transmit an input of the intraocular pressure. The transducer has a sliding transducer mounting sleeve mounting it on the axis. A spring positions the transducer along the axis at a point in response to pressure applied by urging the scleral probe against the sclera. The device includes an annular conductive ring mounted on the mounting sleeve and electrical contacts positioned at a predetermined position on the axis to complete an electrical circuit to generate a signal defining a zone of measurement which has predetermined upper and lower limits of pressure. An output device is mounted in the frame for recoding and/or displaying measurements of pressure by the transducer in the zone of measurement.

10 Claims, 2 Drawing Sheets

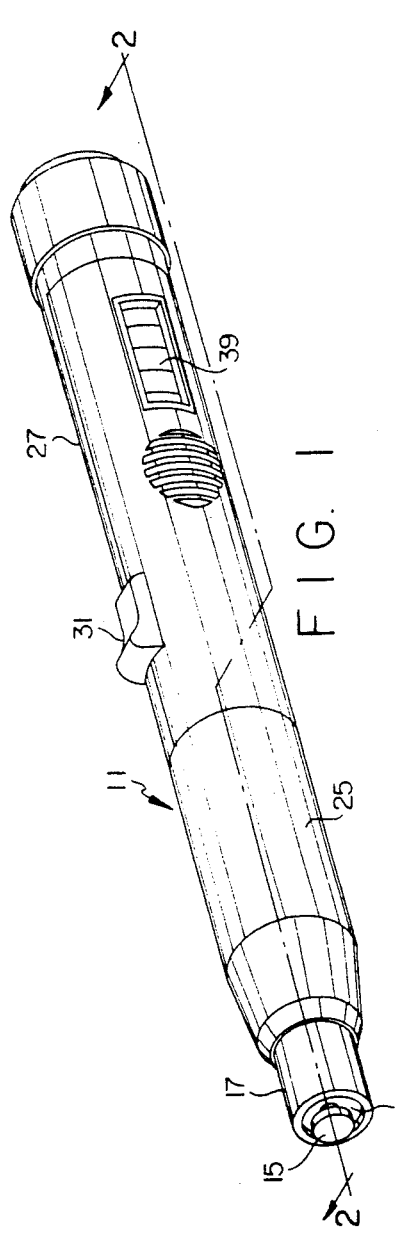
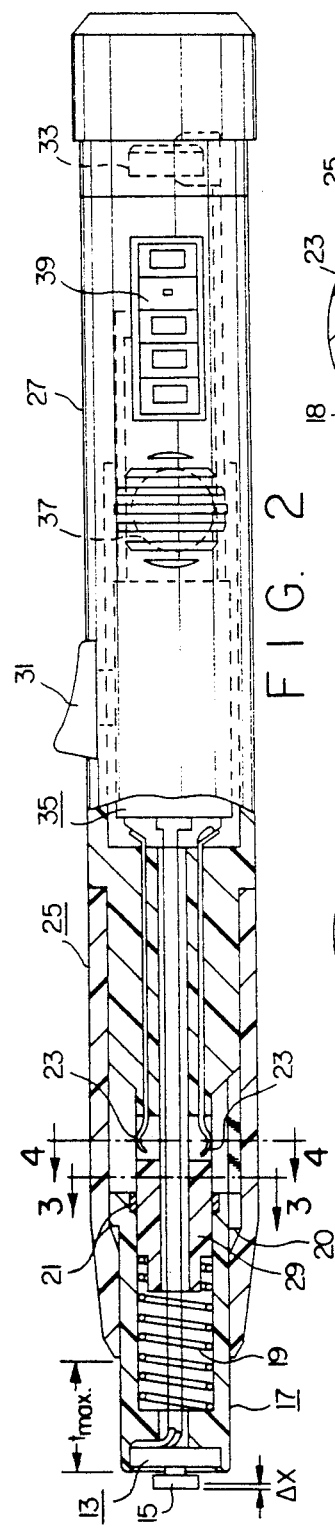
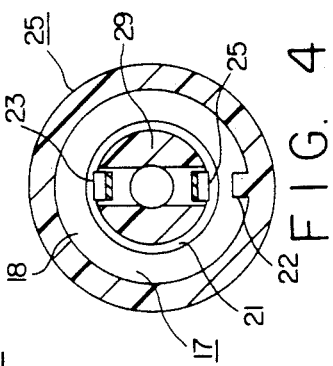
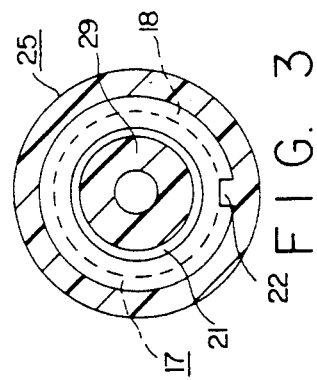

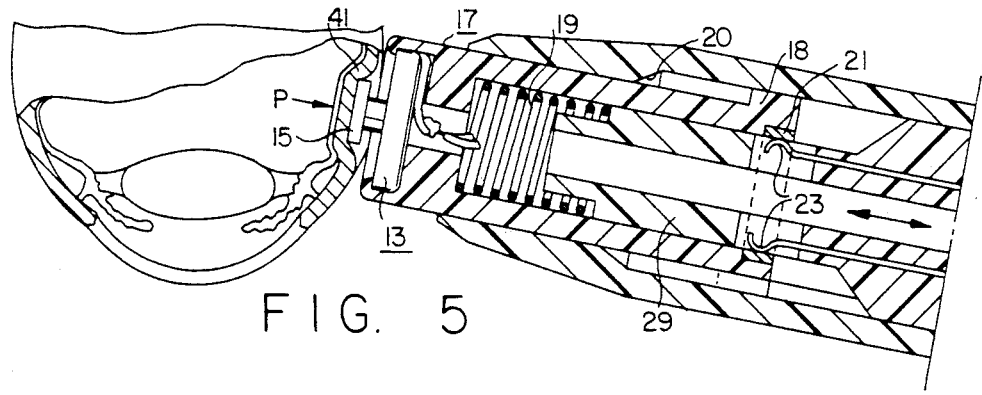
FIG. 5
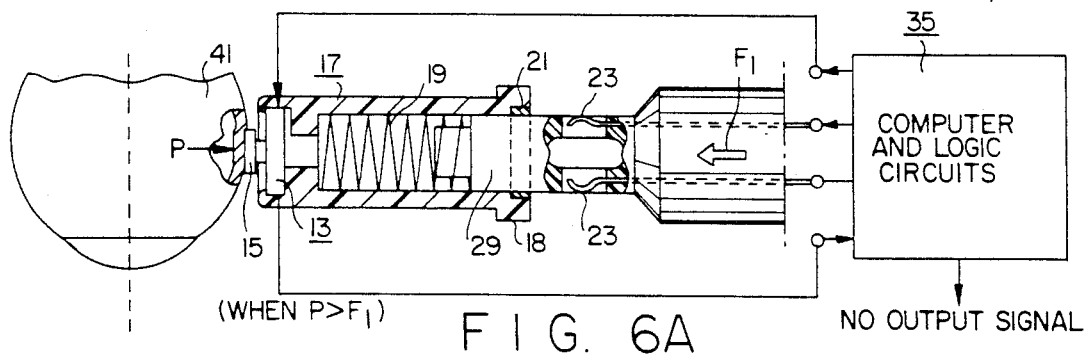
(WHEN P>F₁)  FIG. 6A
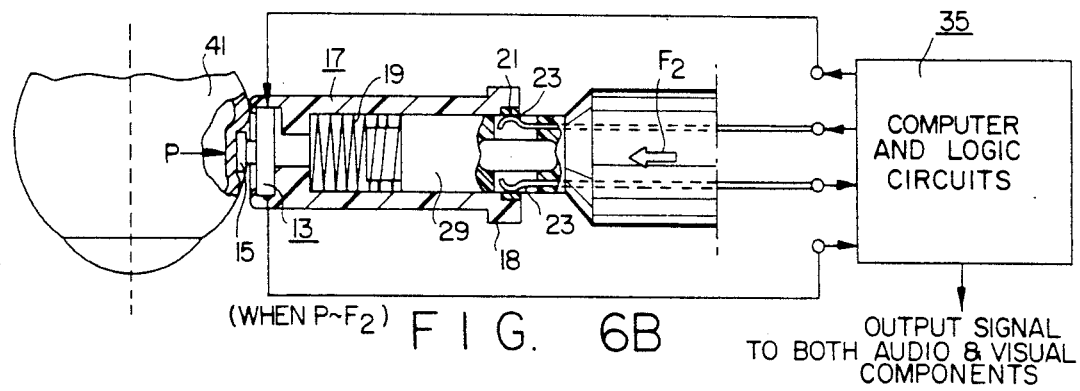
(WHEN P~F₂)  FIG. 6B
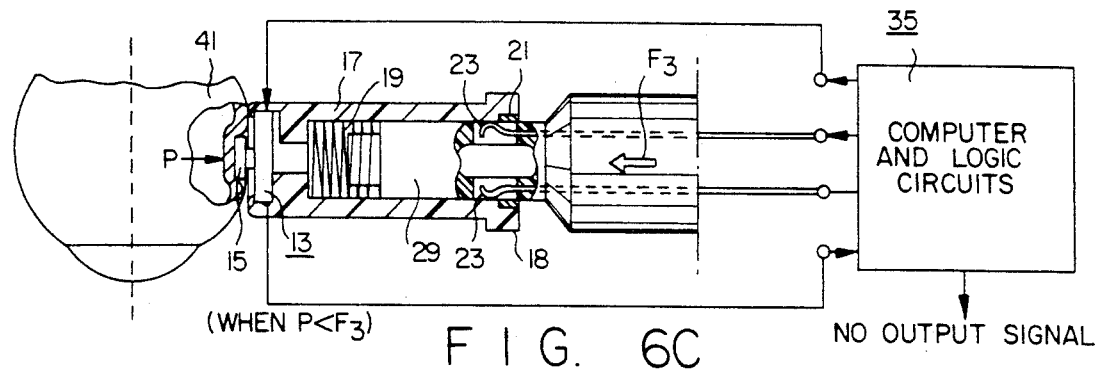
(WHEN P<F₃)  FIG. 6C

HAND HELD INTRAOCULAR PRESSURE RECORDING SYSTEM

FIELD OF THE INVENTION

The present invention relates to a device for recording the intraocular pressure of a person or animal. More particularly, the invention relates to a hand held device which can be placed against the eye to record intraocular pressure of the patient without direct medical personnel supervision.

BACKGROUND OF THE INVENTION

Three to four million persons in the United States suffer from glaucoma to some degree, although only about half of these persons are treated by routine administration of glaucoma medication. Glaucoma is recognized to be the leading cause of blindness in this country.

Typical treatment for glaucoma to reduce the excessive intraocular pressure involves the administration of drugs which operate on the intraocular pressure. These drugs do not have a long term straight line effect on intraocular pressure, however, and individual treatments may be more or less effective at any particular period of time in the treatment cycle. For most glaucoma cases, intraocular pressure varies throughout the day, usually reaching its peak about 3:00 am. The diurnal cycle presents difficulties to the attending physician, who sees the patient at only one relatively short period of time. For this reason, it is difficult for the practitioner to accurately assess the effect of glaucoma medications. The only way this can be done economically is for the patient to make the measurements at home.

At the present time, there is recognition that the cycle of intraocular pressure is diurnal and is subject to several variables. However, no acceptable means presently exists to measure intraocular pressure at home with any degree of safety. The primary difficulty is that all prior art tonometers are designed to measure intraocular pressure through corneal indentation or corneal applination. This requires considerable skill and training along with anesthesia to the cornea.

Other methods such as air tonometry deflect the cornea with a burst of air. This method eliminates the need for anesthesia, but still requires considerable skill. The unit is quite costly and is not portable.

It is therefore an object of this invention to provide a portable tonometer which can be placed against the eye to record intraocular pressure by the patient without direct medical personnel supervision.

Another object of the present invention is to provide such a device which does not require anesthesia, and which is economical to manufacture and easy to use.

Yet another object of the present invention is to provide a device which can be used on the sclera of the eye to measure and record intraocular pressure and which has safety features to prevent too much pressure from being applied.

Other objects will appear hereinafter.

SUMMARY OF THE INVENTION

It has now been discovered that the above and other objects of the present invention may be accomplished in the following manner. Specifically, the present invention provides a device for individual monitoring the intraocular pressure in an eye without anesthesia and with complete safety.

The device of this invention comprises a hand held portable tonometer device for monitoring the intraocular pressure in an eye through the sclera. The device is supported on a tubular frame which forms the handle and which has an axis along which the device operates. The handle supports and contains a pressure transducer for generating intraocular pressure measurements. It is mounted on the axis with a sliding transducer mounting sleeve. The transducer includes a scleral projection for scleral indentation, which is positioned to transmit response to intraocular pressure to provide an input to the transducer.

The transducer sleeve includes an annular conductive ring mounted on the inside of the mounting sleeve. The ring is aligned to complete a circuit upon meeting contact points on the shaft on which the sleeve slides. Also provided is a spring for positioning the transducer along the axis to permit movement along the shaft in response to pressure applied when the scleral projection is urged against the sclera.

The device has a safety feature utilizing the contact element which defines a position of the transducer along the axis to define a zone of measurement which has predetermined upper and lower limits of pressure. The device provides a signal means for providing a first audio signal when the device is operational and a second audio signal when the transducer is in the predetermined zone. The electrical contacts are positioned at a predetermined position on the shaft to engage with the conductive ring to complete an electrical circuit to generate a signal. An output means is also mounted in the frame for displaying relevant measurements of pressure by the transducer, preferably only in the zone of measurement.

BRIEF DESCRIPTION OF THE DRAWINGS

For a more complete understanding of the invention, reference is hereby made to the drawings, in which:

FIG. 1 is an enlarged schematic view, shown in perspective, of a device according to the present invention;

FIG. 2 is an enlarged, side elevational view taken along the line 2,2 in FIG. 1, showing a portion broken away and in section;

FIG. 3 is an enlarged transverse sectional view taken on the line 3,3 of FIG. 2;

FIG. 4 is an enlarged transverse sectional view taken on the line 4,4 of FIG. 2;

FIG. 5 is a greatly enlarged fragmentary sectional plan view showing the device of the present invention in position for use with the left eye, shown in the active or signal sending mode; and FIGS. 6A, 6B, and 6C are schematic sequential views showing the use of the invention.

DETAILED DESCRIPTION OF THE PREFERRED EMBODIMENT

The advantage of the present invention is most importantly that it can be used with minimum skill and training. It is totally self contained and portable and no anesthesia is needed for virtually all patients. This device, shown generally at 11 in the drawings, is the first such device which is capable of being applied to the sclera and which measures the intraocular pressure accurately and in a reproducible manner via scleral indentation.

The hand held tonometer includes a transducer 13 and probe 15 mounted in the tonometer frame 11. Transducer 13 is mounted in a sliding transducer mounting sleeve 17 which fits inside the tonometer along its central axis. Sleeve 17 includes in inwardly facing annular conductive (or metal) ring 21 which is aligned to make electrical contact with a plurality of at least two switch contact points 23. Spring 19 positions the sleeve 17 (and thus the transducer 13 and probe 15) along this same axis.

Transducer 13 is of the type disclosed in my co-pending application entitled PORTABLE, DIURNAL INTRAOCULAR PRESSURE RECORDING SYSTEM, filed Aug. 27, 1991 and having Ser. No. 07/750,528, the disclosure of which is incorporated herein by reference.

The outer housing 25 is formed with an outer barrel sleeve 27 which functions as a handle. Also contained inside the housing 25 is a truncated cylindrical shaft 29. Sleeve 17 slides on shaft 29 freely and is held in position by spring 19 urging the probe 15 in the anterior direction. Sleeve 17 includes a flange 18 which engages limit stop 20 to keep the device assembled.

FIGS. 3 and 4 show the use of a key 22 which is integral with housing 25 to prevent rotation of sleeve 17 and thus prevent breakage of leads to transducer 13.

The housing portion 25 also includes a switch 31 which operates as an off/on switch. The device includes its own power supply, such as battery 33. Battery 33 powers an ohm meter and computer chip unit 35 which functions as will be described. A first signal is produced by speaker 37 when the device is ready for operation and will produce a second signal, such as a plurality of repeated sounds or beeps under certain conditions of use.

This second signal is produced when the ring 21 completes a circuit by being in contact with contact points 23, indicating that the pressure which is forcing the probe against the transducer 13 is that needed to produce useful measurements of intraocular pressure. The probe 15 also forces transducer 13 to compress spring 19 and urge the sleeve 17 along shaft 29 and so that contact between ring 21 and contact points 23 is made.

The housing 25 also encloses a LED readout device 39, of conventional design. LED readout device 39 displays the pressure being measured by the transducer 15 after it has been converted from resistance in ohms into pressure, such as in millimeters of mercury. It is preferred to limit the display of pressure by LED readout device 39 only when electrical contact between ring 21 and contact points 23 is being made. This provides a zone of measurement which has predetermined upper and lower limits of pressure on the spring 19, so that no data is provided at other locations of the sleeve 17 on shaft 29.

Turning now to FIG. 5, the operation of the present invention can be seen. The probe 15 indents the sclera 41 as force is applied by the user by pushing the probe 15 against the eye at the appropriate place, away from the cornea. There is substantially no feeling of pressure and pain is not present at all. Probe 15 is rounded, causing a comfortable and non-abrasive contact with the conjunctiva and sclera. Applination consists of a very small indentation, less than a millimeter in length, and does not cause any permanent change to the sclera.

The intraocular pressure P resists the intrusion and a force is thus directed to the transducer 13. Transducer 13 includes a simple ohm meter and some circuitry to recognize that ring 21 and contact points 23 have completed a circuit.

Application of a consistent and reproducible pressure to the eye is of critical importance and can be done here for the first time. In order to be consistent and reproducible, it is necessary to press the transducer against the eye with the same force each time. It has been observed herein that excess pressure will cause a false elevation of the intraocular pressure, while a lesser pressure will not indent the sclera enough to give reproducible flexion to the ceramic crystal forming the transducer. Either condition will at best result in inconsistence in the intraocular pressure readings and is to be avoided.

The probe 15 is about 3.5 mm in size and is operably connected to a semiconductor strain gauge crystal in transducer 13, such as those used in automatic blood pressure devices. In one embodiment, a $1 \times 2.5$ mm crystal with a nominal resistance of 1125 ohms was attached to a flexible membrane by means of epoxy and thin leads were attached to both ends of the crystal. As current flows through the crystal, and as pressure changes in the intraocular region of the eye, the projection probe 15 reacts to this change in pressure to increase or decrease the bending moment on crystal, thus changing the resistance of the crystal. The ohm meter registers this change and transmits the reading to the LED readout 39

An important part of the present invention is the use of sound or audio signals to assist in the operation of the device and maintain the safety feature, particularly when the patient is using the device alone. A small sound device or speaker 37 which has two purposes in the preferred embodiment. Upon turning the device on, a brief time is needed for the system to warm up. Once the transducer 13 has stabilized, a single tone will be sent by speaker 37 to alert the user that the system is ready to use. Then, as the transducer probe 15 is pressed against the sclera of the eye, a double tone will sound from speaker 37 at that point in the pressure induced movement of sleeve 17 on shaft 29 when ring 21 and contact points 23 are in contact with one another.

This double tone indicates to the user that a valid measurement has been made because the transducer 13 has been subjected to the correct pressure to place the device in the zone of measurement.

FIGS. 6A, 6B, and 6C illustrate the operation of this important safety feature in schematic form. In FIG. 6A, probe 15 is pressing against the sclera and the pressure in the eye is resisting with a force equal to F1. In this case, F1 is less than the pressure P for which the device has been calibrated and for which the contact points 23 will meet ring 21. No data is transmitted to the LED readout 39. As noted above, a lesser pressure will not indent the sclera enough to give reproducible flexion to the ceramic crystal forming the transducer.

In FIG. 6B, probe 15 is also pressing against the sclera and the pressure in the eye is resisting with a force equal to F2. In this case, F2 is the same as the pressure P for which the device has been calibrated and for which the contact points 23 will meet ring 21. Data is transmitted to the LED readout 39 as previously described, as the double tone indicates a successful measurement in the appropriate measurement zone.

In FIG. 6C, probe 15 is pressing against the sclera and the pressure in the eye is resisting with a force equal to F3. F3 is greater than the pressure P for which the device has been calibrated and for which the contact points 23 will meet ring 21. As can be seen, ring 21 is beyond contact points 23 and again no data is transmitted to the LED readout 39. This eliminates the concern that excess pressure will cause a false elevation of the intraocular pressure. When this condition occurs, the double beep tone stops, warning that excessive pressure may be being applied.

With the device of the present invention, it is possible for the first time to measure the intraocular pressure without invasion of the cornea and without anesthetics. It is easy for a patient to be trained to take readings alone and without assistance, yet obtain consistent readings that are of significant value in evaluating treatments and in screening for eye problems such as Glaucoma screening.

While particular embodiments of the present invention have been illustrated and described, it is not intended to limit the invention, except as defined by the following claims.

I claim:

1. A hand held portable tonometer device for monitoring the intraocular pressure in an eye through the sclera, comprising:
   a tubular frame having an axis and forming a handle, said handle including pressure transducer means for generating intraocular pressure measurements, said transducer means including scleral probe means for scleral indentation; biasing means for positioning said transducer means along said axis and for permitting movement thereof along said axis in response to pressure applied by urging said scleral probe means against the sclera;
   contact means at a location along said axis for defining a zone of measurement within which said transducer means must be located to enable measurement of pressure, said zone having limits which correspond to predetermined upper and lower limits of measurable intraocular pressure and for providing a signal when said transducer means is in said zone;
   output means mounted in said frame for displaying measurement of pressure by said transducer means in said zone of measurement upon receipt of said signal.

2. The device of claim 1, wherein said device further includes audio signal means for generating a first audio signal when said device is operational and a second audio signal forming said signal when said transducer means is in said zone.

3. The device of claim 1, wherein said transducer means includes at least one semiconductor strain gauge crystal adapted to generate an electrical resistance which is responsive to intraocular pressure.

4. The device of claim 3, wherein said transducer means includes means for measuring the resistance through said crystal.

5. The device of claim 1, wherein said transducer means includes a sliding transducer mounting sleeve for mounting said transducer means in said handle along said axis and having conductive means, said contact means including electrical contacts positioned at a predetermined position on said axis for engagement with said conductive means to complete an electrical circuit to generate said signal.

6. The device of claim 5, wherein said conductive means comprises an annular conductive ring mounted on said mounting sleeve.

7. A hand held portable tonometer device for monitoring the intraocular pressure in an eye through the sclera, comprising:
   a tubular frame having an axis and forming a handle, said handle including pressure transducer means for generating intraocular pressure measurements and having a sliding transducer mounting sleeve for mounting said transducer means on said axis, said transducer means including scleral probe means for scleral indentation,
   said transducer means including conductive means comprising an annular conductive ring mounted on said mounting sleeve;
   biasing means for positioning said transducer means along said axis and for permitting movement thereof along said axis in response to pressure applied by urging said scleral probe means against the sclera;
   contact means at a location along said axis for defining a zone of measurement within which said transducer means must be located to enable measurement of pressure, said zone having limits which correspond to predetermined upper and lower limits of measurable intraocular pressure and including signal means for providing a first audio signal when said device is operational and a second audio signal when said transducer means is in said zone, said contact means including electrical contacts positioned at a predetermined position on said axis for engagement with said ring to complete an electrical circuit to generate said second signal; and
   output means mounted in said frame for displaying measurements of pressure by said transducer in said zone of measurement upon receipt of said second signal.

8. The device of claim 7, wherein said pressure transducer includes at least one semiconductor strain gauge crystal adapted to generate an electrical resistance which is responsive to intraocular pressure.

9. A method of monitoring the intraocular pressure in an eye through the sclera, comprising the steps of:
   contacting the eye by scleral indentation with a scleral projection means mounted on a pressure transducer means for generating intraocular pressure measurements, said transducer means being positioned to transmit a response to intraocular pressure when said transducer means is located in supports said transducer means, said zone having limits which correspond to predetermined upper and lower limits of measurable intraocular pressure;
   positioning said transducer means along said axis and permitting movement thereof along said axis in response to pressure applied by urging said scleral projection means against the sclera;
   displaying the results of measurements in said zone.

10. The method of claim 9, which further includes the steps of providing a first audio signal when said device is operational and a second audio signal when said transducer means is in said zone.

* * * * *